United States Patent
Barry et al.

(10) Patent No.: US 6,277,126 B1
(45) Date of Patent: Aug. 21, 2001

(54) HEATED VASCULAR OCCLUSION COIL DEVELOPMENT SYSTEM

(75) Inventors: David C. Barry, San Jose, CA (US); Donald K. Jones, Lauderhill; Vladimir Mitelberg, Aventura, both of FL (US)

(73) Assignee: Cordis Neurovascular Inc., Miami Lakes, FL (US)

( * ) Notice: Subject to any disclaimer, the term of this patent is extended or adjusted under 35 U.S.C. 154(b) by 0 days.

(21) Appl. No.: 09/400,680

(22) Filed: Sep. 21, 1999

Related U.S. Application Data

(60) Provisional application No. 60/103,087, filed on Oct. 5, 1998.

(51) Int. Cl.[7] .............................. A61F 2/01; A61M 25/01
(52) U.S. Cl. ........................................... 606/108; 606/200
(58) Field of Search .................................. 606/108, 178, 606/200, 205–208

(56) References Cited

U.S. PATENT DOCUMENTS

| | | | |
|---|---|---|---|
| 4,402,319 | 9/1983 | Handa et al. . | |
| 4,969,458 * | 11/1990 | Wiktor | 606/194 |
| 5,108,407 | 4/1992 | Geremia et al. . | |
| 5,122,136 | 6/1992 | Guglielmi et al. . | |
| 5,217,484 | 6/1993 | Marks . | |
| 5,234,437 * | 8/1993 | Sepetka | 606/108 |
| 5,250,071 * | 10/1993 | Palermo | 606/198 |
| 5,261,916 * | 11/1993 | Engelson | 606/108 |
| 5,263,964 | 11/1993 | Purdy . | |
| 5,334,210 | 8/1994 | Gianturco . | |
| 5,350,397 | 9/1994 | Palermo . | |
| 5,354,295 | 10/1994 | Guglielmi et al. . | |
| 5,382,259 | 1/1995 | Phelps et al. . | |
| 5,423,829 | 6/1995 | Pham et al. . | |
| 5,522,836 | 6/1996 | Palermo . | |
| 5,540,680 | 7/1996 | Guglielmi et al. . | |
| 5,578,074 | 11/1996 | Mirigian . | |
| 5,601,600 | 2/1997 | Ton . | |
| 5,624,449 | 4/1997 | Pham et al. . | |
| 5,634,942 | 6/1997 | Chevillon et al. . | |
| 5,645,564 * | 7/1997 | Northrup et al. | 606/205 |
| 5,690,667 * | 11/1997 | Gia | 606/191 |
| 5,759,161 | 6/1998 | Ogawa et al. . | |
| 5,895,391 * | 4/1999 | Farnholtz | 606/108 |
| 5,925,059 * | 7/1999 | Palermo et al. | 606/191 |
| 5,941,888 * | 8/1999 | Wallace et al. | 606/108 |
| 5,947,962 * | 9/1999 | Guglielmi et al. | 606/32 |
| 5,976,126 * | 11/1999 | Guglielmi | 606/32 |
| 6,077,260 * | 6/2000 | Wheelock et al. | 606/32 |
| 6,083,220 * | 7/2000 | Guglielmi et al. | 606/32 |
| 6,099,546 * | 8/2000 | Gia | 606/191 |
| 6,102,917 * | 8/2000 | Maitland et al. | 606/108 |
| 6,113,622 * | 9/2000 | Hieshima | 606/200 |
| 6,156,061 * | 2/2001 | Wallace et al. | 623/1.11 |
| 6,190,373 * | 2/2001 | Wallace et al. | 623/1.11 |

FOREIGN PATENT DOCUMENTS

| | | |
|---|---|---|
| 4445715 | 6/1996 | (DE) . |
| WO 97/01368 | 1/1997 | (WO) . |
| WO 98/37816 | 9/1998 | (WO) . |
| WO 99/02094 | 1/1999 | (WO) . |

\* cited by examiner

*Primary Examiner*—Gene Mancene
*Assistant Examiner*—Michael B. Priddy
(74) *Attorney, Agent, or Firm*—Henry W. Collins

(57) ABSTRACT

An embolic coil deployment system for placing a coil at a preselected site within a vessel of the human body. The deployment system includes a heating element at the distal end of a delivery member and a heat responsive coupling for holding the coil during positioning of the coil and activation means for releasing the coil at a desired position within the vessel.

33 Claims, 2 Drawing Sheets

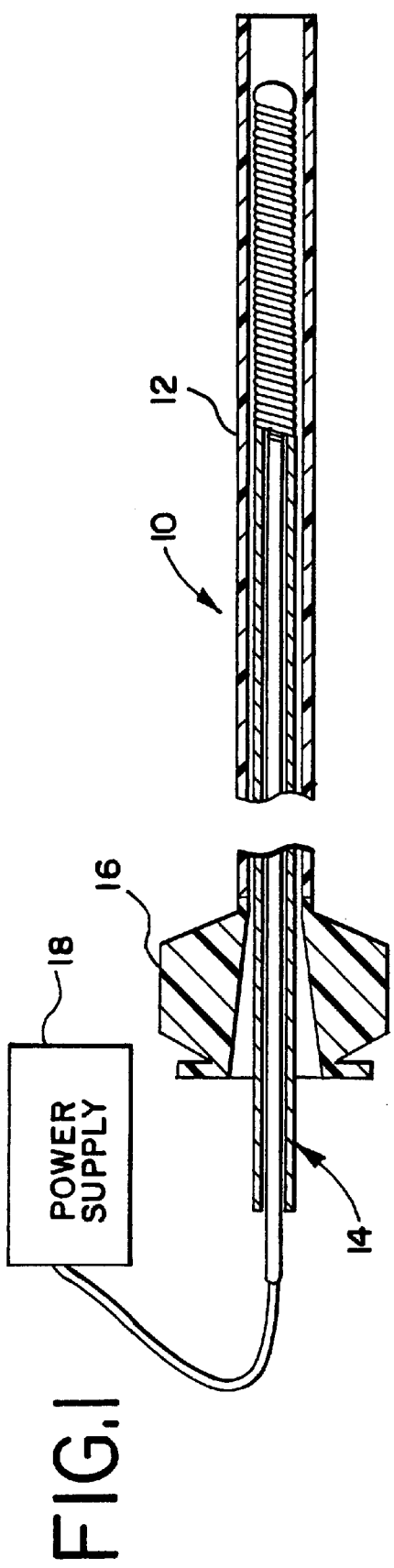
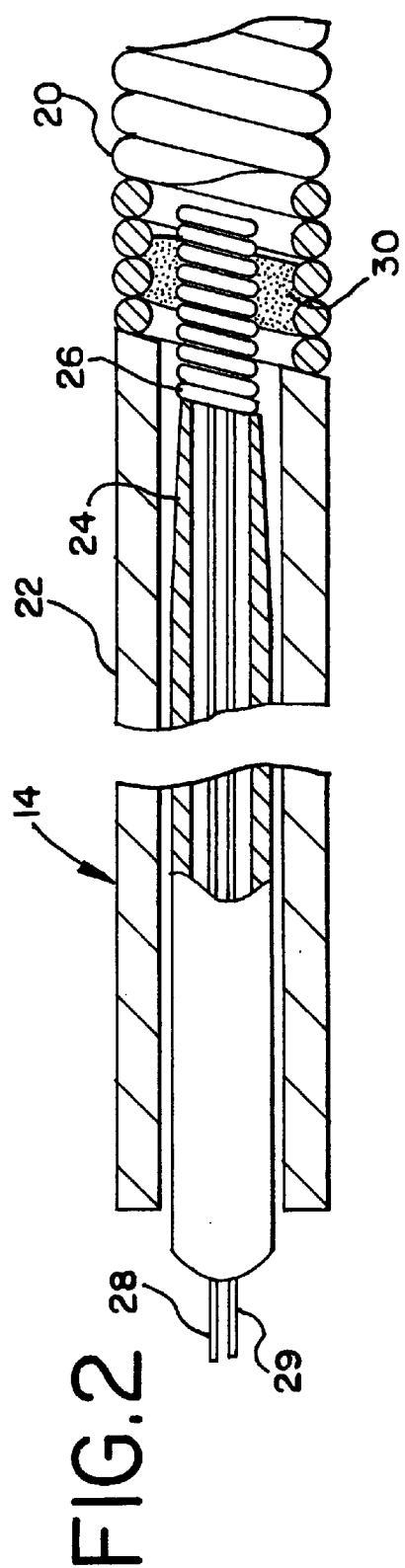

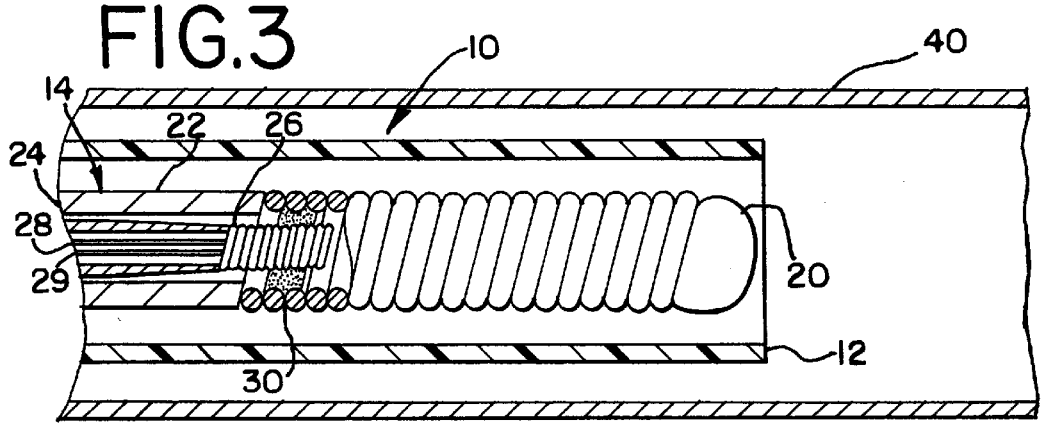
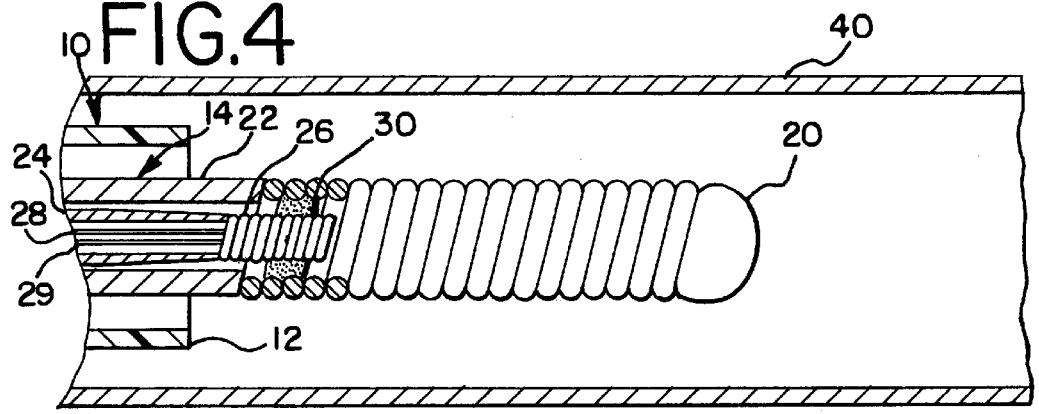
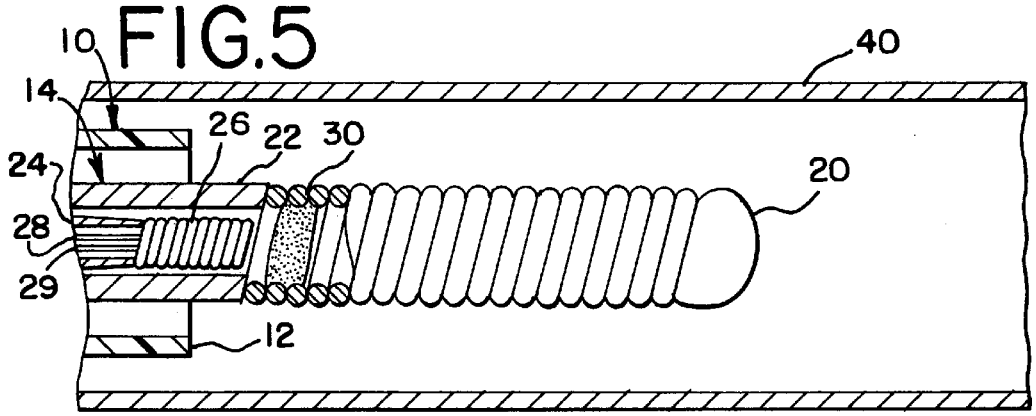
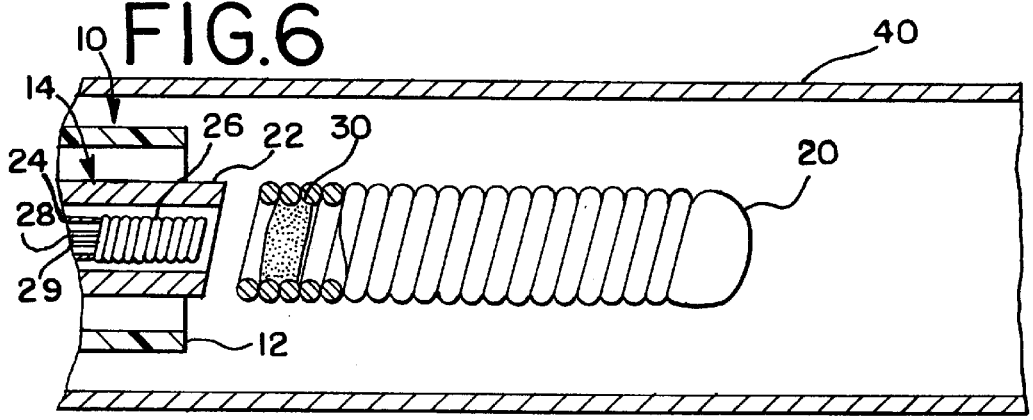

HEATED VASCULAR OCCLUSION COIL DEVELOPMENT SYSTEM

This application claim benefit to Provisional application 60/103,087 filed Oct. 5, 1998.

BACKGROUND OF THE INVENTION

1. Field of the Invention

The present invention relates to a medical device for placing an embolic coil at a preselected location within a vessel of the human body, and more particularly, relates to a flexible delivery member having a heating element and a heat responsive coupling member at the distal tip of the delivery member for holding the embolic coil in order to transport the coil to a desired position within the vessel and release the embolic coil at that position.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected positions within vessel of the human body in order to treat aneurysms, or alternatively, to occlude the blood vessel at the particular location.

Coils which are placed in vessels may take the form of helically wound coils, or alternatively, may be random wound coils, coils wound within other coils or many other such configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven Or Braided Fibrous Coverings." Embolic coils are generally formed of radiopaque metallic materials, such as platinum, gold, tungsten, or alloys of these metals. Often times, several coils are placed at a given location in order to occlude the flow of blood through the vessel by promoting thrombus formation at the particular location.

In the past, embolic coils have been placed within the distal end of the catheter. When the distal end of the catheter is properly positioned the coil may then be pushed out of the end of the catheter with, for example, a guidewire to release the coil at the desired location. This procedure of placement of the embolic coil is conducted under fluoroscopic visualization such that the movement of the coil through the vasculature of the body may be monitored and the coil may be placed at the desired location. With these placements systems there is very little control over the exact placement of the coil since the coil may be ejected to a position some distance beyond the end of the catheter.

Numerous procedures have been developed to enable more accurate positioning of coils within a vessel. Still another such procedure involves the use of a glue, or solder, for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to become detached from the guidewire and released from the catheter system. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be very stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate, relatively stiff element which extends throughout the length of the catheter with resulting stiffness of the catheter.

Still another method for placing an embolic coil is disclosed in co-pending U.S. patent application Ser. No. 09/177,848, entitled, "Embolic Coil Hydraulic Deployment System," filed on Oct. 22, 1998 and assigned to the same assignee as the present patent application. This patent application discloses the use of fluid pressure which is applied to the distal tip of the catheter for expanding the lumen of the catheter in order to release the embolic coil.

SUMMARY OF THE INVENTION

The present invention is directed toward a vascular occlusion coil deployment system for use in placing an embolic coil at a preselected site within a vessel which includes an elongated flexible positioning member having a lumen extending therethrough. An elongated flexible delivery member having a lumen extending therethrough is slidably positioned within the lumen of the positioning member. A heating element is affixed to the distal end of the delivery member and a heat responsive coupling member adhesively bonds the embolic coil to the heating element. The heating element is adapted to be coupled to a source of energy through an energy transmission conductor which extends through the lumen in the delivery member. The heat responsive coupling member, bonding the heating element to the embolic coil, exhibits the characteristic of softening and yielding upon being heated. When energy is applied through the conductor to the heating element, the heating element causes the heat responsive coupling member to yield thereby releasing the embolic coil at the preselected site.

In accordance with another aspect of the present invention, the heating element takes the form of resistive heating coil. At least a portion of this resistive heating coil is bonded to the interior of the heat responsive coupling member to thereby directly apply heat to the coupling when the heating coil is supplied with electrical energy.

In accordance with still another aspect of the present invention, the vascular occlusion coil deployment system for use in placing an embolic coil at a preselected site within a vessel includes an elongated flexible positioning member having a lumen extending therethrough. An elongated flexible delivery member is slidably positioned within the lumen of the positioning member. A heating element is affixed to the distal end of the delivery member and a heat responsive coupling member adhesively bonds the embolic coil to the heating element. The heating element is adapted to be coupled to a source of energy through an energy transmission conductor. The energy transmission conductor extends from the proximal end to the distal end of the delivery member through the lumen of the positioning member and is coupled to the heating element. The heat responsive coupling member, bonding the heating element to the embolic coil, exhibits the characteristic of softening and yielding upon being heated. When energy is applied through the conductor to the heating element, the heating element causes the heat responsive coupling member to yield thereby releasing the embolic coil at the preselected site.

In accordance with still another aspect of the present invention, the energy transmission conductor takes the form of two electrical conductors which extend through the lumen of the delivery member and are connected to the resistive heating coil for applying electrical energy to the coil to thereby cause the coil to become heated.

In accordance with still another aspect of the present invention, the heating element is disposed within a lumen of the embolic coil. The heat responsive coupling member bonds the embolic coil to the heating element. When the heating element is energized the heat responsive coupling member heats. Upon heating the heat responsive coupling member softens thereby reducing its yield strength. This allows the heating element to be retracted into the positioning member breaking the heat responsive coupling member to release the coil.

In accordance with still another aspect of the present invention, the heat responsive coupling member is comprised of a hot melt adhesive. Other suitable materials include low melting temperature metals and metal alloys such as solder. Other suitable materials are those whose yield strength decreases by at least 50 percent when heated to about 65 degrees Celsius.

These aspects of the invention and the advantages thereof will be more clearly understood from the following description and drawings of a preferred embodiment of the present invention:

BRIEF DESCRIPTION OF THE DRAWINGS

FIG. 1 is an enlarged, partially sectioned view of the vascular occlusion coil deployment system of the present invention;

FIG. 2 is an enlarged partially sectioned view showing the coil deployment system prior to placement within a catheter;

FIGS. 3 through 5 are enlarged partially sectioned views illustrating the sequential steps of positioning the vascular coil within a vessel and releasing the coil at a preselected site.

DESCRIPTION OF A PREFERRED EMBODIMENT

FIG. 1 generally illustrates a preferred embodiment of a vascular occlusion coil deployment system 10 of the present invention which is comprised of an elongated flexible catheter 12 which is utilized to position a coil deployment mechanism 14. A Luer connector 16 is connected to the proximal end of the catheter 12 and the coil deployment mechanism 14 is connected to a power supply 18 for applying energy to the coil deployment mechanism 14.

FIG. 2 illustrates in more detail the construction of the coil deployment mechanism 14. More particularly, the deployment mechanism 14 includes an elongated positioning member 22 which is approximately the same length as the outer catheter 12 and which is slidably received by the catheter 12. Positioning member 22 has a lumen extending from its proximal end to its distal end. Coil deployment mechanism 14 also includes a tubular, delivery member 24 which is slidably positioned within the lumen of positioning member 22. Located at the distal end of the delivery member 24 is a heating element 26. The heating element 26 is bonded to the embolic coil 20 by a heat responsive coupling member 30.

The heat responsive coupling member 30 may take the form of any biocompatible adhesive which, upon being heated, softens so that it may be stretched. Preferably, this heat responsive coupling member 30 is comprised of a hot melt adhesive, such as, for example, a hot melt adhesive manufactured by Minnesota Mining and Manufacturing sold under the name Jet Melt, Catalog No. 3783-TC. The temperature required to soften this material is on the order of 63 degrees centigrade.

Also, as illustrated in FIG. 2, the heating element 26 which is preferably a resistively heated coil is coupled to a pair of energy transmission conductors 28, 29. Preferably the energy transmission conductors 28, 29 are electrical conductors also coupled to power supply 18. Upon application of an electrical current to the pair of conductors 28, 29 the heating element 26 begins to heat to thereby cause the heat responsive coupling member 30 to increase in temperature. As the heat responsive coupling member 30 becomes warm it softens and has a lower yield strength, thus, breaking when the delivery member 24 is retracted to release the embolic coil 20.

More particularly, and as illustrated in FIGS. 3 through 6, the vascular occlusion coil deployment system 10 is inserted into a blood vessel 40 and is moved to a position within the blood vessel 40 to a position where it is desirable to place the embolic coil 20. When the catheter 12 has been positioned at a location slightly proximal of the preselected site for placement of the embolic coil (FIG. 4), the coil deployment mechanism 14 is pushed out of the distal end of the catheter 12 and electrical energy is then applied to the heating element 26 to thereby soften the heat responsive coupling member 30. Once the heat responsive coupling member 30 softens, the delivery member 24 is retracted, thus disengaging the heating element 26 from embolic coil 20 breaking the adhesive bond of heat responsive coupling member 30. As the delivery member 24 is retracted, there is no longer engagement between the heating element 26 and the embolic coil 20 and the coil is released.

Finally, and as illustrated in FIG. 6, the coil deployment mechanism 14 is withdrawn back into the catheter 12 and the embolic coil 20 remains in its deployed position.

With the vascular occlusion coil deployment system of the present invention it is possible to place an embolic coil very precisely at a desired location within a vessel. Once the coil has been placed in a preselected location by catheter, the deployment mechanism may be activated by applying energy to a coil release mechanism to thereby cause the coil to be released and deposited at a desired location.

As is apparent, there are numerous modifications of the preferred embodiment described above which will become readily apparent to one skilled in the art, such as many variations and modifications of the deployment system including many different variations of the heating element, many variations of energy sources for heating the adhesive such as optical, radiofrequency, and acoustical, many variations of energy transmission conductors such as optical fiber, and many variations of heat softening adhesives.

These modifications would be apparent to those having ordinary skill in the art to which this invention relates and are intended to be within the scope of the claims which follow.

That which is claimed is:

1. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member having a lumen extending therethrough and being positioned within the lumen of the positioning member and having proximal and distal ends;

a heating element mounted on the distal end of the delivery member;

an energy transmission conductor extending through the lumen of the delivery member and extending from the proximal end to the distal end of the delivery member wherein said energy transmission conductor is an electrical conductor, said energy transmission conductor being coupled to said heating element; and, a heat responsive coupling member adhesively bonded to both the heating element and to the embolic coil, said heat responsive coupling member exhibits the characteristic of, upon being heated, releasing its adhesive bond whereby upon applying energy through the energy transmission conductor to the heating element, the heating element causes the heat responsive coupling member to release the embolic coil at the pre-selected site.

2. A vascular occlusion coil deployment system as defined in claim 1, wherein said heat responsive coupling member between said heating element and said embolic coil is positioned within the lumen of said embolic coil.

3. A vascular occlusion coil deployment system as defined in claim 1, wherein said energy is electrical energy.

4. A vascular occlusion coil deployment system as defined in claim 1, wherein said heating element is an electrically heated element.

5. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member having a lumen extending therethrough and being positioned within the lumen of the positioning member and having proximal and distal ends;

a heating element mounted on the distal end of the delivery member, wherein said heating element is an electrically heated coil;

an energy transmission conductor extending through the lumen of the delivery member and extending from the proximal end to the distal end of the delivery member, said energy transmission conductor being coupled to said heating element; and, a heat responsive coupling member adhesively bonded to both the heating element and to the embolic coil, said heat responsive coupling member exhibits the characteristic of, upon being heated, releasing its adhesive bond whereby upon applying energy through the energy transmission conductor to the heating element, the heating element causes the heat responsive coupling member to release the embolic coil at the pre-selected site.

6. A vascular occlusion coil deployment system as defined in claim 5, wherein said heat responsive coupling member is formed of a solid material, wherein the yield strength is reduced at least 50 percent when heated to about 65 degrees Celsius, between said heating element and said embolic coil.

7. A vascular occlusion coil deployment system as defined in claim 6, wherein said solid material is formed of a polymer.

8. A vascular occlusion coil deployment system as defined in claim 6, wherein said solid material is formed of a metal alloy.

9. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member being positioned within the lumen of the positioning member and having proximal and distal ends;

a heating element mounted on the distal end of the delivery member;

an energy transmission conductor extending through the lumen of the positioning member, wherein said energy transmission conductor is an electrical conductor, said energy transmission conductor being coupled to said heating element; and, a heat responsive coupling member bonded to both the heating element and to the embolic coil, said heat responsive coupling member exhibits the characteristic of, upon being heated, having a reduced adhesive force whereby upon applying energy through the energy transmission conductor to the heating element, the heating element causes the heat responsive coupling member to release the embolic coil at the pre-selected site.

10. A vascular occlusion coil deployment system as defined in claim 9, wherein said heat responsive coupling member between said heating element and said embolic coil is positioned within the lumen of said embolic coil.

11. A vascular occlusion coil deployment system as defined in claim 9, wherein said energy is electrical energy.

12. A vascular occlusion coil deployment system as defined in claim 9, wherein said heating element is an electrically heated element.

13. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member being positioned within the lumen of the positioning member and having proximal and distal ends;

a heating element mounted on the distal end of the delivery member, wherein said heating element is an electrically heated coil;

an energy transmission conductor extending through the lumen of the positioning member, said energy transmission conductor being coupled to said heating element; and, a heat responsive coupling member bonded to both the heating element and to the embolic coil, said heat responsive coupling member exhibits the characteristic of, upon being heated, having a reduced adhesive force whereby upon applying energy through the energy transmission conductor to the heating element, the heating element causes the heat responsive coupling member to release the embolic coil at the pre-selected site.

14. A vascular occlusion coil deployment system as defined in claim 13, wherein said heat responsive coupling member is formed of a solid material, wherein the yield strength is reduced at least 50 percent when heated to about 65 degrees Celsius, between said heating element and said embolic coil.

15. A vascular occlusion coil deployment system as defined in claim 14, wherein said solid material is formed of a polymer.

16. A vascular occlusion coil deployment system as defined in claim 14, wherein said solid material is formed of a metal alloy.

17. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member being slidably positioned within the lumen of the positioning member and having proximal and distal ends;

a heating element mounted on the distal end of the delivery member;

an energy transmission conductor extending through the lumen of the positioning member wherein said energy transmission conductor is an electrical conductor, said energy transmission conductor being coupled to said heating element; and, a heat responsive coupling member bonded to both the heating element and to the embolic coil, said heat responsive coupling member exhibits the characteristic of, upon being heated, softening thereby reducing its yield strength whereby upon applying energy through the energy transmission conductor to the heating element the heating element causes the heat responsive coupling member to break thereby releasing the embolic coil at the pre-selected site.

18. A vascular occlusion coil deployment system as defined in claim 17, wherein said heat responsive coupling member between said heating element and said embolic coil is positioned within the lumen of said embolic coil.

19. A vascular occlusion coil deployment system as defined in claim 17, wherein said energy is electrical energy.

20. A vascular occlusion coil deployment system as defined in claim 17, wherein said heating element is an electrically heated element.

21. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member being slidably positioned within the lumen of the positioning member and having proximal and distal ends;

a heating element mounted on the distal end of the delivery member, wherein said heating element is an electrically heated coil;

an energy transmission conductor extending through the lumen of the positioning member, said energy transmission conductor being coupled to said heating element; and, a heat responsive coupling member bonded to both the heating element and to the embolic coil, said heat responsive coupling member exhibits the characteristic of, upon being heated, softening thereby reducing its yield strength whereby upon applying energy through the energy transmission conductor to the heating element the heating element causes the heat responsive coupling member to break thereby releasing the embolic coil at the pre-selected site.

22. A vascular occlusion coil deployment system as defined in claim 21, wherein said heat responsive coupling member is formed of a solid material, wherein the yield strength is reduced at least 50 percent when heated to about 65 degrees Celsius, between said heating element and said embolic coil.

23. A vascular occlusion coil deployment system as defined in claim 22, wherein said solid material is formed of a polymer.

24. A vascular occlusion coil deployment system as defined in claim 22, wherein said solid material is formed of a metal alloy.

25. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member having a lumen extending therethrough and being positioned within the lumen of the positioning member and having proximal and distal ends;

a heating element mounted on the distal end of the delivery member;

a non-optical fiber energy transmission conductor extending through the lumen of the delivery member and extending from the proximal end to the distal end of the delivery member, said energy transmission conductor being coupled to said heating element; and, a heat responsive coupling member adhesively bonded to both the heating element and to the embolic coil, said heat responsive coupling member exhibits the characteristic of, upon being heated, releasing its adhesive bond whereby upon applying energy through the energy transmission conductor to the heating element, the heating element causes the heat responsive coupling member to release the embolic coil at the pre-selected site.

26. A vascular occlusion coil deployment system as defined in claim 25, wherein said heating element is an electrically heated element.

27. A vascular occlusion coil deployment system as defined in claim 25, wherein said heat responsive coupling member is formed of a solid material, wherein the yield strength is reduced at least 50 percent when heated to about 65 degrees Celsius, between said heating element and said embolic coil.

28. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member being positioned within the lumen of the positioning member and having proximal and distal ends;

a heating element mounted on the distal end of the delivery member;

a non-optical fiber energy transmission conductor extending through the lumen of the positioning member, said energy transmission conductor being coupled to said heating element; and, a heat responsive coupling member bonded to both the heating element and to the embolic coil, said heat responsive coupling member exhibits the characteristic of, upon being heated, having a reduced adhesive force whereby upon applying energy through the energy transmission conductor to the heating element, the heating element causes the heat responsive coupling member to release the embolic coil at the pre-selected site.

29. A vascular occlusion coil deployment system as defined in claim 28, wherein said heating element is an electrically heated element.

30. A vascular occlusion coil deployment system as defined in claim 28, wherein said heat responsive coupling member is formed of a solid material, wherein the yield strength is reduced at least 50 percent when heated to about 65 degrees Celsius, between said heating element and said embolic coil.

31. A vascular occlusion coil deployment system for use in placing a coil at a pre-selected site within a vessel comprising:

an elongated flexible positioning member having a lumen extending therethrough and having proximal and distal ends;

an embolic coil;

an elongated flexible delivery member being slidably positioned within the lumen of the positioning member and having proximal and distal ends;

a heating element mounted on the distal end of the delivery member;

a non-optical fiber energy transmission conductor extending through the lumen of the positioning member, said energy transmission conductor being coupled to said heating element; and, a heat responsive coupling member bonded to both the heating element and to the embolic coil, said heat responsive coupling member exhibits the characteristic of, upon being heated, softening thereby reducing its yield strength whereby upon applying energy through the energy transmission conductor to the heating element the heating element causes the heat responsive coupling member to break thereby releasing the embolic coil at the pre-selected site.

32. A vascular occlusion coil deployment system as defined in claim 31, wherein said heating element is an electrically heated element.

33. A vascular occlusion coil deployment system as defined in claim 32, wherein said heat responsive coupling member is formed of a solid material, wherein the yield strength is reduced at least 50 percent when heated to about 65 degrees Celsius, between said heating element and said embolic coil.

* * * * *

UNITED STATES PATENT AND TRADEMARK OFFICE
CERTIFICATE OF CORRECTION

PATENT NO. : 6,277,126 B1
DATED : August 21, 2001
INVENTOR(S) : Barry et al.

It is certified that error appears in the above-identified patent and that said Letters Patent is hereby corrected as shown below:

<u>Title page,</u>
Item [54], "HEATED VASCULAR OCCLUSION COIL DEVELOPMENT SYSTEM" should be -- HEATED VASCULAR OCCLUSION COIL DEPLOYMENT SYSTEM --

Signed and Sealed this

Fourteenth Day of May, 2002

*Attest:*

JAMES E. ROGAN
*Attesting Officer*     *Director of the United States Patent and Trademark Office*